(12) United States Patent
Marquez et al.

(10) Patent No.: US 7,009,050 B2
(45) Date of Patent: Mar. 7, 2006

(54) 5-SUBSTITUTED PYRIMIDINE DERIVATIVES OF CONFORMATIONALLY LOCKED NUCLEOSIDE ANALOGUES

(75) Inventors: Victor E. Marquez, Montgomery Village, MD (US); Pamela L. Russ, Great Falls, VA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 172 days.

(21) Appl. No.: 10/346,762

(22) Filed: Jan. 15, 2003

(65) Prior Publication Data

US 2005/0282837 A1 Dec. 22, 2005

Related U.S. Application Data

(63) Continuation of application No. PCT/US01/23246, filed on Jul. 24, 2001.

(60) Provisional application No. 60/220,934, filed on Jul. 26, 2000.

(51) Int. Cl.
  *C07D 239/54* (2006.01)
  *C07D 239/553* (2006.01)
  *A61K 31/513* (2006.01)
  *A61P 31/22* (2006.01)

(52) U.S. Cl. ............... 544/309; 544/313; 544/317; 514/274

(58) Field of Classification Search ........... 544/309, 544/313, 317; 514/274
See application file for complete search history.

(56) References Cited

U.S. PATENT DOCUMENTS

| 5,629,454 A | 5/1997 | Marquez et al. ........... 568/327 |
| 5,840,728 A | 11/1998 | Marquez et al. ........... 514/261 |
| 5,869,666 A | 2/1999 | Marquez et al. ........... 544/276 |

FOREIGN PATENT DOCUMENTS

| WO | WO 95/08541 | 3/1995 |
| WO | WO 98/05662 | 2/1998 |

OTHER PUBLICATIONS

"Fields Virology, Third Ed.", B. N. Fields et al eds., Lippincott-Raven, Philadelphia, 1996 ,p. 431.*
Salmon, S.E. et al "Principles of Cancer Therapy" in "Cecil Textbook of Medicine, 20th Edition", W.B. Saunders, Philadelphia, 1996, pp. 1036-1049.*
Balasubramanian, B.N. et al, "Recent Developments in Cancer Cytoxics" in "Annual Reports in Medicinal Chemistry, vol. 33", Academic Press, San Diego, 1998, pp. 151-159.*
Miller, D.M. "The Future of Oncology" in "Cecil Textbook of Medicine, 20th Edition", W.B. Saunders, Philadelphia, 1996, pp. 1071-1077.*
Grignet-Debrus et al., (2000) *Comparative in vitro and in vivo cytotoxic activity of (E)-5-(2-bromovinyl)-2'-deoxyuridine (BVDU) and its arabinosyl derivative, (E)-5-(2-bromovinyl)-1-β-D-arabinofuranosyluracil (BvaraU), against tumor cells expressing either the Varicella zoster or the Herpes simplex virus thymidine kinase*, Cancer Gene Therapy, vol. 7, No. 2, pp. 215-223.
Marquez et al., (1996) *Nucleosides with a Twist. Can Fixed Forms of Sugar Ring Pucker Influence Biological Activity in Nucleosides and Oligonucleotides?*, Journal of Medicinal Chemistry, vol. 39, No. 19, pp. 3739-3747.

* cited by examiner

*Primary Examiner*—Thomas C. McKenzie
(74) *Attorney, Agent, or Firm*—Knobbe, Martens, Olson & Bear, LLP

(57) ABSTRACT

The embodiments described herein concern 5-substituted pyrimidine derivatives of conformationally locked nucleoside analogues and to the use of these derivatives as antiviral and anti-cancer agents. The compounds are of the formula:

wherein B is uracil-1-yl or cytosin-1-yl having a 5-substituent selected from halogen, alkyl, alkenyl, and alkynyl, with the proviso that where B is uracil-1-yl, the 5-substituent is not methyl. The compounds are useful in the treatment of Herpes simplex virus (HSV).

37 Claims, No Drawings

5-SUBSTITUTED PYRIMIDINE DERIVATIVES OF CONFORMATIONALLY LOCKED NUCLEOSIDE ANALOGUES

CROSS REFERENCE TO RELATED APPLICATIONS

This application is a continuation of international application number PCT/US01/23246, and claims the benefit of priority of international application number PCT/US01/23246 having international filing date of Jul. 24, 2001, designating the United States of America and published in English, which claims the benefit of priority of U.S. provisional patent application No. 60/220,934, filed Jul. 26, 2000; both of which are hereby expressly incorporated by reference in their entireties.

FIELD OF THE INVENTION

Aspects of the present invention relate to 5-substituted pyrimidine derivatives of conformationally locked nucleoside analogues and to the use of these derivatives as antiviral and anti-cancer agents.

BACKGROUND OF THE INVENTION

It has been recognized that incorporating modified non-functional analogues of DNA substituents during replication is an effective method for terminating DNA replication and in turn preventing generation of viable progeny. Recent studies have demonstrated that modified and synthetic riboses and nitrogenous bases have anti-viral activity against varying viral genera depending on the modification. There is a constant need for effective anti-viral and anti-cancer agents.

SUMMARY OF THE INVENTION

Aspects of the present invention concern 5-substituted pyrimidine derivatives of conformationally locked nucleoside analogues and the use of these derivatives as anti-viral and anti-cancer agents. Several embodiments include:

A 5-substituted pyrimidine derivative of a conformationally locked nucleoside analogue comprising the formula:

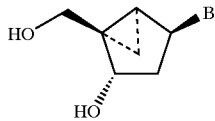

wherein B is a 5-substituted derivative of uracil, except when the 5-substituent is methyl, or cytosine.

The nucleoside analogue above, wherein the 5-substituent is a halogen, alkyl, alkene, or alkyne group.

The nucleoside analogue above, wherein the 5-substituent is F, Cl, Br, I, CH$_2$CH$_3$, CH=CH$_2$, C≡CH, C≡CHCH$_3$, CH=CHF, CH=CHCl, CH=CHBr, or CH=CHI.

The nucleoside analogue above, wherein B is a 5-substituted derivative of uracil and the 5-substituent is a member of the group consisting of F, Cl, Br, I, CH$_2$CH$_3$, CH=CH$_2$, C≡CH, C≡CHCH$_3$, CH=CHF, CH=CHCl, CH=CHBr, and CH=CHI.

The nucleoside analogue above, wherein B is a 5-substituted derivative of cytosine and the 5-substituent is a member of the group consisting, of F, Cl, Br, I, CH$_2$CH$_3$, CH=CH$_2$, C≡CH, C≡CHCH$_3$, CH=CHF, CH=CHCl, CH=CHBr, and CH=CHI.

The nucleoside analogue above consisting of Bromine 5-substituted uracil nucleoside.

The nucleoside analogue above consisting of Iodine 5-substituted uracil nucleoside.

The nucleoside analogue above consisting of Bromovinyl 5-substituted uracil nucleoside.

Aspects of the invention also concern approaches to test the nucleoside analogs, described above, for antiviral activity. Some embodiments include:

A method of testing any one of the nucleoside analogues above for anti-viral activity comprising the step of measuring its effect in a cytopathogenic effect inhibition assay.

A method of testing any one of the nucleoside analogues above for antiviral activity comprising the step of measuring its effect in a virus plaque reduction assay.

Additional embodiments include methods of making the nucleoside analogs above. Some embodiments include:

A method of making one of the nucleoside analogues above comprising the step of combining a 5-substituted pyrimidine moiety with a bicyclo[3.1.0]hexane template.

A method of making one of the nucleoside analogue aboves comprising the step of proceeding via Mitsunobu coupling with a 5-substituted base.

Still more embodiments concern methods of reducing the replication of a virus in an individual in need thereof. Some embodiments include:

A method of reducing replication of a virus in an individual in need thereof, comprising the step of administering to said individual an effective antiviral amount of any one of the compounds above in a pharmaceutically acceptable carrier.

The method above, wherein said virus is selected from the group consisting of Herpes simplex virus (HSV), Varicella zoster virus (VZV), Epstein Barr virus (EBV), and Cytomegalovirus (CMV).

The method above, wherein said administering step is parenteral, enteral, topical, or sustained or directed release.

The method above, wherein said effective antiviral amount is about 100 mg to 500 mg per unit dosage.

A method of terminating DNA-chain elongation in the cells of an individual in need thereof, comprising the step of administering to said cells of said individual an effective DNA-chain elongation terminating amount of any one of the compounds above in a pharmaceutically acceptable carrier.

The method above, wherein said cells are modified to express a Herpes simplex virus thymidine kinase.

Pharmaceuticals comprising the nucleoside analogues described above are also embodiments. For example, some embodiments concern a pharmaceutical composition comprising any one of the nucleoside analogs above in a pharmaceutically acceptable excipient. Packs comprising any one of the nucleoside analogs above in unit dosage form are also embodiments.

DETAILED DESCRIPTION OF THE INVENTION

Marquez et al., J. Med. Chem. 39:3739 (1996) describe purine and pyrimidine nucleoside analogs having natural bases attached to a bicyclo[3.1.0]hexane pseudosugar template. Grignet-Debrus et al., Cancer Gene Therapy 7:215 (2000) describe modified bases, particularly 5-substituted uracils, which are characteristic moieties of antiviral nucleosides when attached to common sugars. The substitution of the modified bases of Grignet-Debrus et al. for the natural bases of Marquez et al. produces pyrimidine analogs that are completely surprising, because the incorporation of these known bases to a bicyclo[3.1.0]hexane template provides antivirally active compounds that are potent like their nucleoside counterparts and the carbocyclic analogues with a plain cyclopentane ring.

Aspects of the present invention are directed to 5-substituted pyrimidine derivatives of conformationally locked nucleoside analogues, and to methods of using these derivatives as anti-viral and anti-cancer agents.

5-substituted pyrimidine derivatives of conformationally locked nucleoside analogues have the formula:

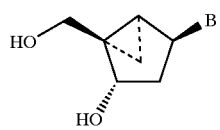

Where B is a 5-substituted derivative of uracil, except when the 5-substituent is methyl, and cytosine. The 5-substituent is understood to be a halogen, alkyl, alkene, or alkyne group. In preferred embodiments, the 5-substituent is F, Cl, Br, I, $CH_2CH_3$, $CH=CH_2$, $C\equiv CH$, $C\equiv CCH_3$, $CH=CHF$, $CH=CHCl$, $CH=CHBr$ or $CH=CHI$.

In one embodiment, B is a 5-substituted derivative of uracil, except when the 5-substituent is methyl, and the 5-substituent is a member of the group consisting of F, Cl, Br, I, $CH_2CH_3$, $CH=CH_2$, $C\equiv CH$, $C\equiv CCH_3$, $CH=CHF$, $CH=CHCl$, $CH=CHBr$ and $CH=CHI$.

In an another embodiment, B is a 5-substituted derivative of cytosine, and the 5-substituent is a member of the group consisting of F, Cl, Br, I, $CH_2CH_3$, $CH=CH_2$, $C\equiv CH$, $C\equiv CCH_3$, $CH=CHF$, $CH=CHCl$, $CH=CHBr$ and $CH=CHI$.

5-substituted pyrimidine derivatives of conformationally locked nucleoside analogues may be tested for antiviral activity by a variety of methods known in the art. One assay is the cytopathogenic effect inhibition assay. Another assay is the virus plaque reduction assay.

The cytopathogenic effect inhibition assay proceeds generally as follows. Marquez et al., J. Med. Chem. 39:3739 (1996). Low-passage (3–10) human foreskin fibroblast (HFF) cells are trypsinized, counted, and seeded into 96-well tissue culture plates at a cell concentration of $2.5 \times 10^4$ cells in 0.1 mL of minimal essential media (MEM) supplemented with 10% fetal bovine serum media (FBS). The cells are then incubated for 24 h at 37° C. in a 5% $CO_2$–95% air, 90% humidified atmosphere. The media are then removed, and 100 µL of MEM containing 2% FBS is added to all but the first row. In the first row, 125 µL of media containing the experimental compound are added in triplicate wells. Media alone are added to both cell and virus control wells. The compound in the first row of wells is then diluted serially 1:5 throughout the remaining wells by transferring 25 µL using the Cetus Liquid Handling Machine. The plates are then incubated for 1 h, and 100 µL of the appropriate virus concentration is added to each well, excluding cell control wells, which receive 100 µL of MEM. The viral concentration utilized is 1000 PFU/well. The plates are then incubated at 37° C. in a $CO_2$ incubator for 3 days. After the incubation period, media are aspirated and the cells stained with a 0.1% crystal violet solution for 30 min. The stain is then removed, and the plates are rinsed with tap water until all excess stain is removed. The plates are allowed to dry for 24 h and then read on a BioTek Multiplate Autoreader.

The virus plaque reduction assay proceeds generally as follows. Marquez et al., J. Med. Chem. 39:3739 (1996). On the date of the assay, the drug is made up at 2 times the desired concentration in 2×MEM and then serially diluted 1:5 in 2×MEM to give six concentrations of drug. The drug concentrations utilized are usually 200 down to 0.06 µg/mL. The virus to be used is diluted in MEM containing 10% FBS to a desired concentration which will give 20–30 plaques/well. The media are then aspirated from the wells, and 0.2 mL of virus is added to each well in duplicate with 0.2 mL of media being added to drug toxicity wells. The plates are then incubated for 1 hr with shaking every 15 min. After the incubation period, an equal amount of 1% agarose is added to an equal volume of each drug dilution. This gives a final drug concentration beginning with 100 and ending with 0.03 µg/mL and a final agarose overlay concentration of 0.5%. The drug agarose mixture is applied to each well in 2 mL volume, and the plates are incubated for 3 days, after which the cells are stained with a 1.5 solution of neutral red. At the end of the 4–6 h incubation period, the stain is aspirated, and plaques are counted using a stereomicroscope at 10× magnification.

The 5-substituted pyrimidine derivatives of conformationally locked nucleoside analogues have been found to possess valuable pharmacological properties. They have an anti-viral effect. This effect can be demonstrated using the cytopathogenic effect inhibition assay and the virus plaque reduction assay.

The conformationally locked (North)-methanocarbathymine is a potent and selective antiherpes agent, 30 times more potent than acyclovir against Herpes simplex virus-1 (HSV-1) and Herpes simplex virus-2 (HSV-2) in the plaque reduction assay. Since the 5-substitutent in pyrimidine nucleosides is a modulator of antiherpes activity, such as in the very effective antiviral compound bromovinyluridine (BVDU), we decided to explore a set of substituents of 5-substituted uracils (Br, 1, CH=CH—Br) on this new class of carbocyclic nucleosides built on a bicyclo[3.1.0]hexane template. The series was limited only to the conformationally locked North analogues since the South conformational antipode of methanocarbathymine was found to be inactive. The syntheses of these compounds can proceed linearly from the corresponding carbocyclic amine via the uracil analogue or by a convergent approach via Mitsunobu coupling with the 5-substituted base.

Tables 1, 2, and 3 demonstrate antiviral activity of 5-substituted uracils (Br, I, CH=CH—Br) attached to a bicyclo [3.1.0]hexane template relative to the corresponding known active controls using the cytopathogenic effect inhibition assay and the virus plaque reduction assay. These results predict that combining any 5-substituted uracil moiety, not just when the 5-substitutuent is methyl, with a bicyclo[3.1.0] hexane pseudosugar will result in compounds with antiviral activity. These results additionally predict that the combination of any 5-substituted pyrimidine moiety with a bicyclo [3.1.0]hexane template will also will result in compounds with antiviral activity.

Thus, embodiments also relate to a method for the treatment of a viral infection, which comprises administering to a patient having a viral infection a therapeutically effective amount of an anti-viral composition comprising at least one of a 5-substituted conformationally locked nucleoside analogue. The method of the invention typically comprises mixing the analogue with a pharmaceutically acceptable carrier to facilitate the administration of the anti-viral composition. Preferably, the anti-viral compositions are used to treat Herpes simplex virus (HSV), Varicella zoster virus (VZV), Epstein Barr virus (EBV), and Cytomegalovirus (CMV).

TABLE 1

Antiviral activity against herpes viruses HSV-1 and HSV-2

| Compound | HSV-1 (HFF)[a] CPE inhib. $EC_{50}$[b] (μg/ml) | HSV-1 (HFF) CPE inhib. $CC_{50}$[c] (μg/ml) | SI[d] | HSV-2 (HFF) CPE inhib. $EC_{50}$ (μg/ml) | HSV-2 (HFF) CPE inhib. $CC_{50}$ (μg/ml) | SI | HSV-1 (HFF) plaque red'n $EC_{50}$ (μg/ml) | HSV-1 (HFF) plaque red'n $CC_{50}$ (μg/ml) | SI | HSV-2 (HFF) plaque red'n $EC_{50}$ (μg/ml) | HSV-2 (HFF) plaque red'n $CC_{50}$ (μg/ml) | SI |
|---|---|---|---|---|---|---|---|---|---|---|---|---|
| (N)-MCdIU (4) | >100 | >100 | 0 | 3.3 | >100 | 30.3 | | | | | | |
| (N)-MCdBrU (3) | 0.39 | >100 | >256 | 0.70 | >100 | >142 | 0.03 | >100 | 3333 | 0.12 | >100 | 833 |
| (N)-MCBVDU (5) | 2.2 | >100 | >45 | >100 | >100 | 0 | | | | | | |
| ACV[e] (control) | 0.5 | | | | | | | | | | | |

[a]HFF = human foreskin fibroblast;
[b]$EC_{50}$ = inhibitory concentration required to reduce virus induced cytopathogenic effect (CPE) or virus plaques by 50%;
[c]$CC_{50}$ = cytotoxic concentration that produces 50% of cell growth;
[d]SI = selectivity index ($CC_{50}/EC_{50}$);
[e]acyclovir

TABLE 2

Antiviral activity against vaccinia and pox

| Compound | Vaccinia (HFF)[a] CPE inhib. $EC_{50}$[b] (μg/ml) | Vaccinia (HFF) CPE inhib. $CC_{50}$[c] (μg/ml) | SI[d] | Vaccinia (HFF) Plaque red'n $EC_{50}$ (μg/ml) | Vaccinia (HFF) Plaque red'n $CC_{50}$ (μg/ml) | SI | Cowpox (HFF) CPE inhib. $EC_{50}$ (μg/ml) | Cowpox (HFF) CPE inhib. $CC_{50}$ (μg/ml) | SI | Cowpox (HFF) Plaque red'n $EC_{50}$ (μg/ml) | Cowpox (HFF) Plaque red'n $CC_{50}$ (μg/ml) | SI |
|---|---|---|---|---|---|---|---|---|---|---|---|---|
| (N)-MCdBrU (3) | 0.64 | >100 | >156 | 2.6 | >100 | 38.5 | 11.5 | >100 | 8.7 | 3.4 | >100 | 29.4 |

[a]HFF = human foreskin fibroblast;
[b]$EC_{50}$ = inhibitory concentration required to reduce virus induced cytopathogenic effect (CPE) or virus plaques by 50%;
[c]$CC_{50}$ = cytotoxic concentration that produces 50% of cell growth;
[d]SI = selectivity index ($CC_{50}/EC_{50}$);
[e]acyclovir

TABLE 3

Antiviral activity against VZV

| | Antiviral activity (Plaque reduction) $EC_{50}$ (μM)[a] | | | | Cytotoxicity (μM) | |
|---|---|---|---|---|---|---|
| | TK + VZV | | TK − VZV | | Cell | |
| Compound | YS strain | OKA strain | 07/1 strain | YS/R strain | Morphology (MCC)[b] | $CC_{50}$[c] |
| (N)-MCdBrU (3) | 0.03 | 0.89 | 107 | 37 | >200 | >200 |
| (N)-MCdIU (4) | 012 | 0.16 | >5 | 3 | >5 | >200 |
| (N)-MCBVDU (5) | 0.007 | 0.005 | >5 | >5 | >5 | >200 |
| ACV (control) | 2.4 | 2.4 | 30 | 19 | >200 | 488 |
| BVDU (control) | 0.008 | 0.005 | >150 | >150 | >150 | >400 |

[a]$EC_{50}$ = inhibitory concentration required to reduce virus plaques by 50%;
[b]MCC = minimum cytotoxic concentration that causes microscopically detectable alteration of cell morphology;
[c]$CC_{50}$ = cytotoxic concentration that produces 50% of cell growth.

Methods of Synthesis

Scheme 1

Scheme 1 illustrates how to synthesize a bicyclo[3.1.0] hexane uracil nucleoside (2) starting with a bicyclo[3.1.0] hexane template (6).

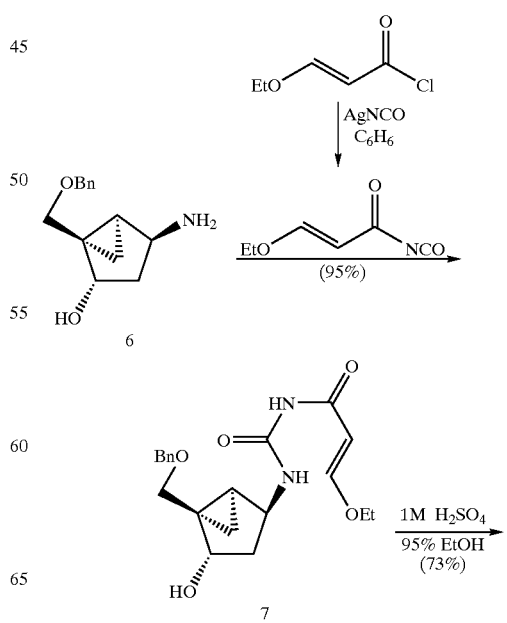

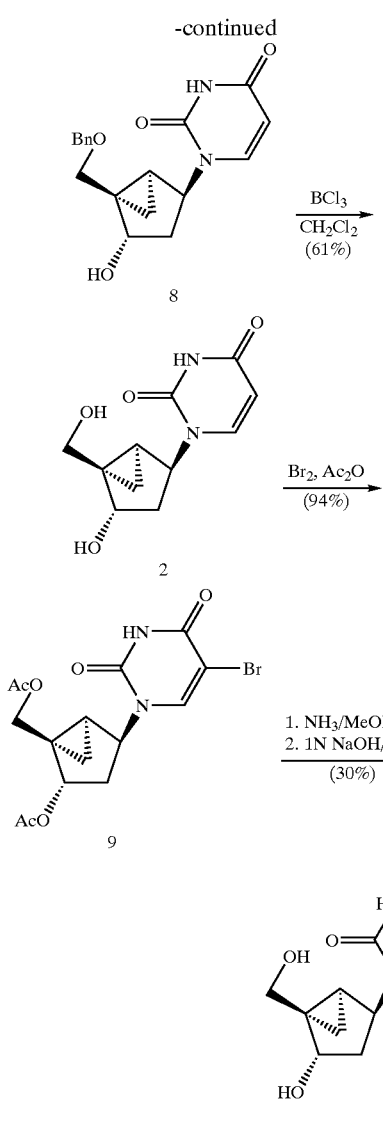

Compound 7

To 3-ethoxy acrylchloride (2.41 g, 0.018 m) in 50 mL benzene was added AgNCO (6.0 g, 0.036 m) which had been dried for 2 h at 100° C. under vacuum. The mixture was refluxed under Ar for 0.75 h. Cooled to RT. 40 mL of the organic supernatant was added dropwise to a solution of 6 (2.08 g, 0.009 m) in DMF (50 mL) which had been cooled in an ice/salt bath under Ar. Reaction stirred overnight as bath warmed to RT. Concentrated in vacuo. 7 (3.19 g, yellow "glass", 95%) was obtained by silica gel flash chromatography using 50% EtOAc/hexane and EtOAc. A small portion of 7 was purified for analysis Analyzed for $C_{20}H_{26}N_2O_5 \cdot 0.25H_2O$ Mw 378.94

Calc: C, 63.39; H, 7.05; N, 7.39

Found: C, 63.56; H, 6.93; N, 7.50

63.50 7.00 7.48

Compound 8

To 7 (3.19 g, 0.085 m) dissolved in 95% EtOH (100 mL) was added 1M $H_2SO_4$ (100 mL) and the reaction refluxed for 1 h. The EtOH was removed, the resulting mixture neutralized with 2N NaOH to pH7, and extracted with chloroform (3×100 mL). The combined extracts were washed 2×100 mL saturated $NaHCO_3$, dried over $MgSO_4$ and concentrated in vacuo. 8 (2.02 g, 73% colorless foam, $\alpha]_D$=+59(C, 0.16, MeOH)) was obtained by silica gel flash chromatography using EtOAc.

Analyzed for $C_1H_{20}N_2O_4 \cdot 0.25H_2O$ Mw 332.88

Calc: C, 64.95; H, 6.21; N, 8.42

Found: C, 65.12; H 6.33; N 8.20

65.02 6.27 8.14

Compound 2

To 8 (0.164 g, 0.5 mmole) in $CH_2Cl_2$ (30 mL) cooled to −78° C. was added 1M $BCl_3/CH_2Cl_2$ and the reaction stirred cold under Ar for 1 h. MeOH (5 mL) added, the reaction concentrated in vacuo and reconcentrated with methanol (2×5 mL). 2 (0.073 g, white solid) was obtained by silica gel flash chromatography using $CHCl_3$ and 10% $MeOH/CHCl_3$ Note: this is a known compound (U.S. Pat. No. 5,840,728).

Scheme 2

Scheme 2 illustrates how to synthesize a Bromine (Br) 5-substituted uracil nucleoside (3) starting with the bicyclo [3.1.0]hexane uracil nucleoside (2).

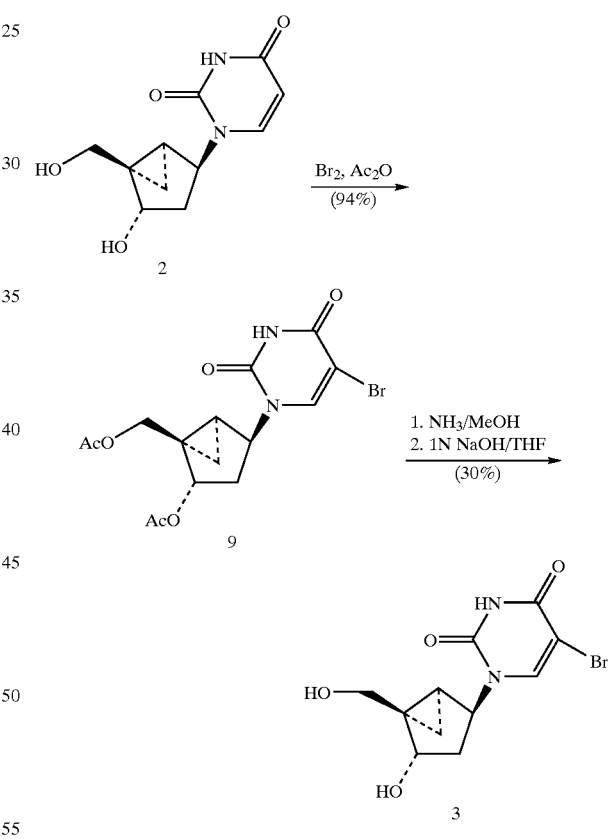

Compound 9

2 (0.073 g, 0.31 mmole) was dissolved in $Ac_2O$ (2 mL) with warming and cooled to RT under Ar. $Br_2$ (0.02 mL, 0.33 mmole) was added dropwise, the reaction stirred at RT for 0.5 h and stored in the refrigerator overnight. The $Ac_2O$ was removed in vacuo and reconcentrated with toluene (3×5 mL). Treatment of the orange residue with water gave 0.062 g white solid and 0.050 g orange semisolid both containing crude 9. Reasonably pure 9 (0.117 g, colorless foam, $R_F$ 0.86 (EtOAc, MH+401/403, 94%)) was obtained by silica gel flash chromatography using 50% EtOAc/hexane and EtOAc.

Compound 3

9 (0.111 g, 0.277 mmole) was dissolved in 3 mL of saturated ammonia in methanol, kept at RT overnight and then heated at 50° C. for another 24 h. The solid obtained by removal of the NH₃MeOH($R_F$ 0.32, 15% MeOH/CHCl₃) was found by NMR to contain one acetate group. To this solid dissolved in THF (2.5 mL) was added 1N NaOH (0.2 mL) and the reaction stirred at RT. Acetic acid (20 μL) was added and the reaction concentrated in vacuo. Crude 3 was obtained by C-18 reverse phase flash chromatography using water and methanol. Pure 3 (0.026 g, mp 218–219° C., α]$_D$=+18.2 (C, 0.11, MeOH), MH⁺317/319, 30%) was obtained by silica gel flash chromatography using a step gradient of CHCl₃ and 10% MeOH/CHCl₃.

Analyzed for C₁₁H₁₃N₂O₄Br Mw 317.14
Calc: C, 41.66; H, 4.13; N, 8.83
Found: C, 42.14; H, 4.22; N, 8.54
42.19 4.31 8.57

Scheme 3A

Scheme 3A illustrates how to synthesize a Iodine (I) 5-substituted uracil nucleoside (4) starting with the bicyclo[3.1.0]hexane uracil nucleoside (2).

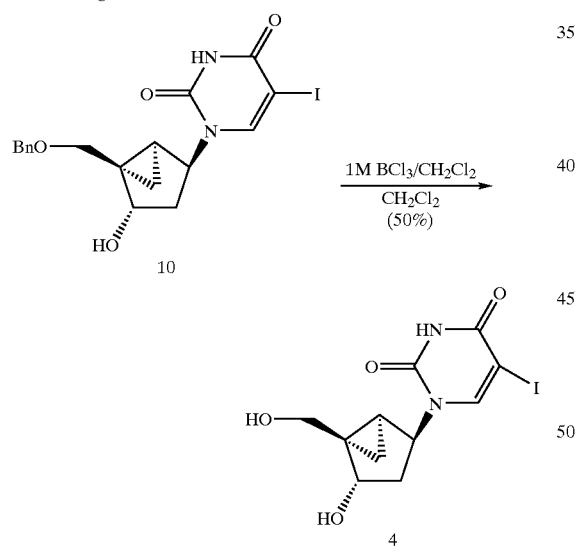

Compound 10

A stirred solution of 8 (0.164 g, 0.5 mmole), I₂ (0.254 g, 1.0 mmole) and 1N HNO₃ (0.5 mL) in dioxane (5 mL) was heated at 100° C. for 1 h. Concentrated in vacuo and reconcentrated with ethanol (3×5 mL) and chloroform (3×10 mL). 10 (0.191 g off-white solid, 84%, mp 85–88° C., $R_F$ 0.6 (EtOAc)) was obtained by silica gel flash chromatography using a step gradient of 50% EtOAc/hexane and EtOAc.

Analyzed for C₁₈H₁₉N₂O₄·0.5H₂O Mw 463.28
Calc: C, 46.67; H, 4.35; N, 6.06
Found: C, 46.24; H, 4.22; N, 5.89
46.33 4.18 5.92

Compound 4

To a solution of 10 (0.072 g, 0.16 mmole) in CH₂Cl₂ (10 mL) cooled in dry ice/acetone was added 1M BCl₃/CH₂Cl₂ (1.6 mL). After 1 h methanol (3 mL) was added to the cold reaction. The reaction was concentrated in vacuo and reconcentrated with methanol (3×5 mL). Purification by silica gel slash chromatography using CHCl₃ and 5% MeOH/CHCl₃ gave a colorless residue which, on treatment with Et₂O gave 4 (0.028 g, 50%, mp 229–230° C., α]$_D$=−1.5 (C, 0.13, MeOH) MH⁺365).

Scheme 3B

Scheme 3B illustrates how to synthesize a Iodine (1) 5-substituted uracil nucleoside (4) via Mitsunobu coupling with the 5-substituted base (11).

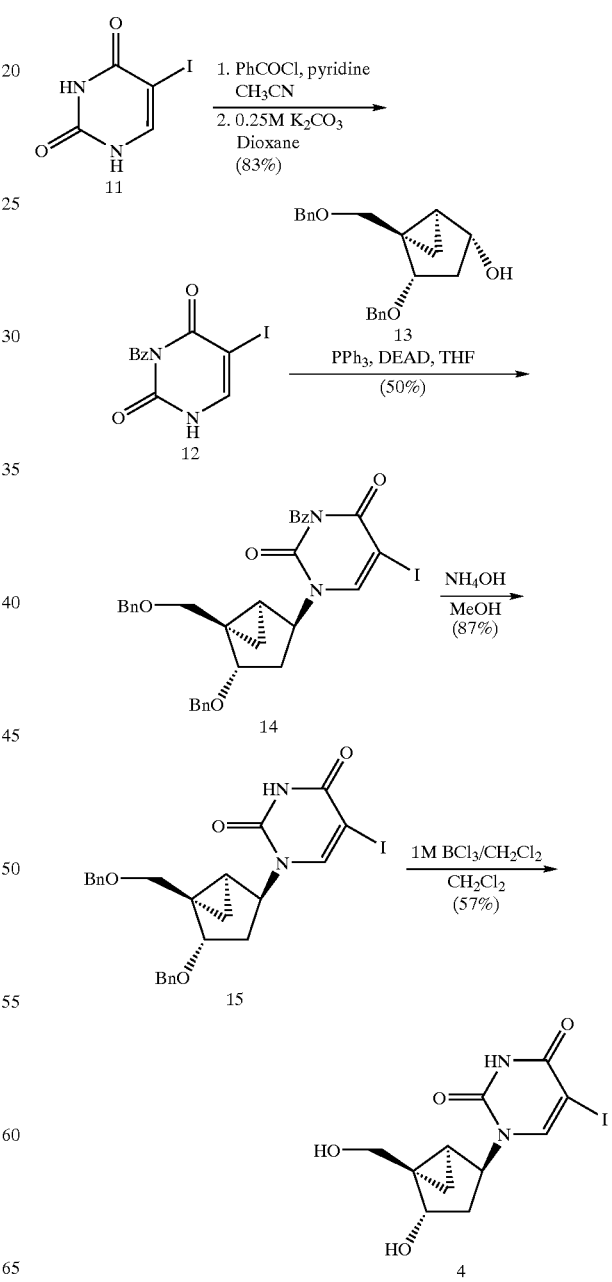

Compound 12

Benzoyl chloride (1.0 mL, 0.009 m) was added dropwise to a stirred suspension of 11 (0.95 g, 0.004 m) in pyridine (4 mL) and acetonitrite (10 mL) under Ar at RT for 4 days. The reaction was concentrated in vacuo and reconcentrated with toluene (3×20 mL). Dioxane (15 mL) and 0.25 m $K_2CO_3$ (15 mL) were added and the reaction stirred at RT for 2 h. The dioxane was removed in vacuo and the mixture was diluted with water (20 mL). The solid was isolated and recrystallized from 95% ethanol to give 12 (1.13 g, 84%, mp 205–207° C.).

Compound 14

A solution of DEAD (0.52 mL, 3.31 nmole) in THF (20 mL) was added dropwise to a stirred solution of 12 (1.34 g, 3.92 mmole), 13 (0.536 g, 165 mmole) and $Ph_3P$ (0.866 g, 3.31 mmole) in THF (50 mL) under Ar. The reaction was stirred overnight at RT. Concentrated in vacuo. Crude 14 was isolated by silica gel flash chromatography using a step gradient of hexane and 25% EtOAc/hexane. Pure 14 (0.117 g, 11%) was obtained by silica gel flash chromatography using a step gradient of hexane, 25% and 30% EtOAc/hexane as a white solid/glass. $R_F$ 0.77(50% EtAc/hexane).

Analyzed for $C_{32}H_{29}N_2O_5$ I Mw 648.50

Calc: C, 59.27; H, 4.51; N, 4.32

Found: C, 59.33; H, 4.59; N, 4.31

Compound 15

14 (0.110 g, 0.17 mmole), conc. $NH_4OH$ (1 mL), and MeOH (14 mL) were stirred for 1 h at RT. Concentrated in vacuo. 15 (0.080 g, 87%) a white solid was obtained by silica gel flash chromatography using a step gradient of hexane, 25% and 50% EtOAc/hexane.

Analyzed for $C_{25}H_{25}N_2O_4$ I Mw 544.39

Calc: C, 55.16; H, 4.63; N, 5.16

Found: C, 55.18; H, 4.62; N, 5.19

Compound 4

To a solution of 15 (0.031 g, 0.057 mmole) in $CH_2Cl_2$ (10 mL) cooled in a dry ice/acetone bath was added 1.2 mL 1M $BCl_3/CH_2Cl_2$ and the reaction stirred cold for 1 h. MeOH (3 mL) was added and the reaction concentrated in vacuo. Reconcentrated three times with methanol (5 mL). 4 (0.012 g 57% mp 226–227 C, $\alpha]_D$=−3 [c,0.1, MeOH]) was obtained by silica gel flash chromatography using a step gradient of $CHCl_3$ and 5% $MeOH/CHCl_3$ and then recrystallization from $MeOH/CHCl_3$.

Analyzed for $C_{11}H_{13}N_2O_4I \cdot 01H_2O$ Mw 365.94

Calc: C, 36.10; H, 3.65; N, 7.66

Found: C, 36.08; H, 3.74; N, 7.44

36.13 3.69 7.37

Scheme 4

Scheme 4 illustrates how to synthesize a Bromovinyl (CH=CH—Br) 5-substituted uracil nucleoside (5) starting with the bicyclo[3.1.0]hexane uracil nucleoside (2).

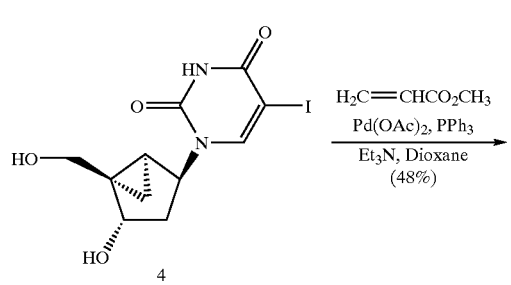

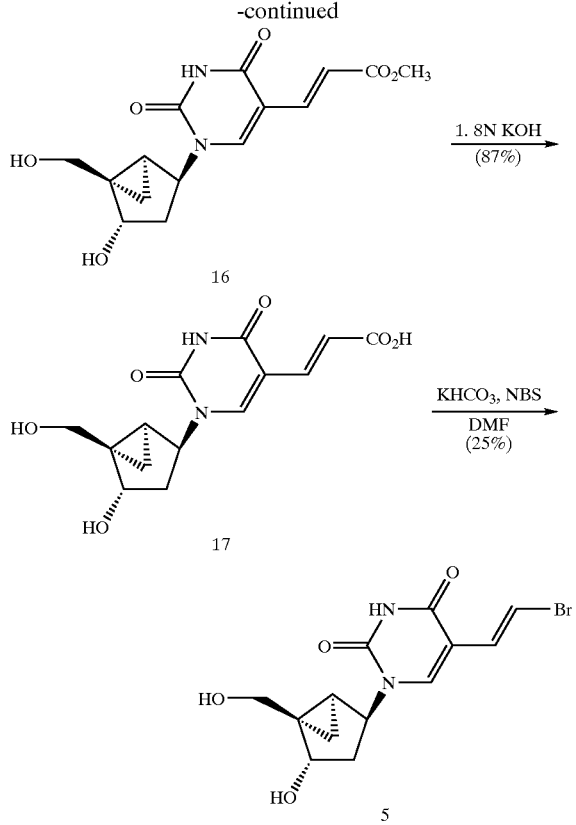

Compound 16

Pd II(OAc)$_2$ (0.0055 g, 0.025 mmole) and $Ph_3P$ (0.013 g, 0.050 mmole) were dissolved in dioxane (1 mL) in a vial fitted with a teflon lined cap. Let stand for 10 min during which time the solution turned red. $Et_3N$ (0.055 mL, 0.40 mmole), then methylacrylate (0.110 ml, 1.24 mm), then 4 (0.089 g, 0.247 mmole), and finally dioxane (2 mL) were added, the vial sealed and heated at 78° C. for 4 h. Reaction repeated on same scale. The two reactions were combined and concentrated in vacuo. Initial purification by silica gel flash chromatography using a step gradient of $CHCl_3$, 5% $MeOH/CHCl_3$ and 10% $MeOH/CHCl_3$ separated the unreacted 4 from product 16. Using the same chromatography conditions unreacted 4 (0.054 g, mp 224–226) was recovered. Treatment of the crude product with EtOAc (2 mL) gave 16 (0.076 g, 48%) white crystals, mp 240–241° C. $R_F$=0.54 (15% $MeOH/CHCl_3$), $\alpha]_D$−2.4 [c, 2.3, MeOH]).

Analyzed for $C_{15}H_{18}N_2O_6 \cdot 0.25H_2O$ Mw 326.32

Calc: C, 55.21; H, 5.56; N, 8.58

Found: C 55.14; H, 5.69; N, 8.50

55.15 5.60 8.53

Ref: Herdewijn, P. et al, J. Med. Chem. 1985, 28, 550–555.

Compound 17

16 (0.165 g, 0.512 mmole) was stirred in 1.8N KOH (2 mL) overnight. The reaction was acidified with HCl (conc) to pH2 and the solid was isolated by vacuum filtration. The filtrate was concentrated in vacuo and the residue triturated with MeOH. The supernatant was concentrated in vacuo. The combined solids were dissolved in boiling methanol, filtered, and the filtrate concentrated in vacuo to give 17 (0.137 g, white solid, 87%, mp 240° C. (dec). Used with no further purification.

Compound 5

To a mixture of 17 (0.12 g, 0.41 mmole) in DMF (2.5 mL) was added $KHCO_3$ (0.118 g, 1.18, 1.18 mmole) and then dropwise a solution of NBS (0.072 g, 0.41 mmole) in DMF (1 mL). Stirred at RT for 2.5 h. Insolubles were removed by filtration and the filtrate concentrated in vacuo. Crude 5 was isolated by silica gel flash chromatography using a step gradient of $CHCl_3$, 5% $MeOH/CHCl_3$ and 10% $MeOH/CHCl_3$. 5 was purified further by silica gel flash chromatography using a step gradient of $CH_2C$ 12, 5% i-PrOH/$CH_2Cl_2$ and 10% i-PrOH/$CH_2Cl_2$ and finally by reverse phase C-18 silica gel flash chromatography using water and 20% MeOH/water to give pure 5 (0.035 g, 25% off-white solid, mp 120–122° C. $[\alpha]_D$=−23[c, 0.13, MeOH], $MH^+$343/345).

Analyzed for $C_{13}H_{15}N_2O_4$ Br·0.5$H_2$0 Mw 352.19

Calc: C, 44.33; H, 4.58; N, 7.95

Found: C, 44.47; H, 4.29; N, 7.76

44.40; 4.36 7.78

Method of Using

The 5-substituted pyrimidine derivatives of conformationally locked nucleoside analogues have been found to possess valuable pharmacological properties. They have an anti-viral effect. This effect can be demonstrated using the cytopathogenic effect inhibition assay and the virus plaque reduction assay (Tables 1, 2, and 3).

Thus, these analogues can be used to treat viral infections, specifically infections of DNA viruses including members of the Herpesviridae family, especially Herpes simplex virus (HSV), Varicella zoster virus (VZV), Epstein Barr virus (EBV), and Cytomegalovirus (CMV) as well as members of the Poxyiridae family.

In addition, the analogues can be used in cancer gene therapy. Gene-mediated prodrug activation is a therapeutic approach for the treatment of cancer. It relies on the transfer into tumor cells of a "suicide" gene that encodes an enzyme which, unlike the cellular enzymes, is able to convert a nontoxic prodrug into a toxic metabolite. The most widely investigated system combines the thymidine kinase (tk)-encoding gene of herpes simplex virus (HSV) and ganciclovir (GCV), a nucleoside analogue. The enzyme converts the prodrug into a metabolite that is incorporated into the DNA of dividing cells, which leads to termination of DNA-chain elongation, resulting in death of the cell. We contemplate the replacement of GCV by 5-substituted conformationally locked nucleoside analogues in the field of suicide gene therapy.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application, which do not deleteriously react with the active compounds. Suitable pharmaceutically acceptable to carriers include but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

Sustained or directed release compositions can be formulated, e.g., by inclusion in liposomes or incorporation into an epidermal patch with a suitable carrier, for example DMSO. It is also possible to freeze-dry these compounds and use the lyophilizates obtained, for example, for the preparation of products for injection.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

Generally, the compounds of this invention are dispensed in unit dosage form comprising 100 mg to 500 mg in a pharmaceutically acceptable carrier per unit dosage. They are incorporated in topical formulations in concentrations of about 2% to 10% by weight.

The dosage of the compositions according to this invention generally is 10 mg/kg/day to 50 mg/kg/day, when administered to patients, e.g., humans, to treat viral infections analogously to the known agent acyclovir.

It will be appreciate that the actual preferred amounts of active compound in a specific case will vary according to the specific compound being utilized, the compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

Having now fully described the invention, it will be understood to those of ordinary skill in the art that the same can be performed with a wide and equivalent range of conditions, formulations, and other parameters without affecting the scope of the invention or any embodiment thereof. All patents and publications cited herein are fully incorporated by reference hereby in their entirety.

What is claimed is:

1. A conformationally locked nucleoside analogue comprising the formula:

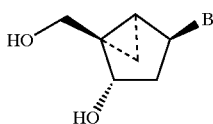

wherein B is
a 5-substituted cytosin-1-yl and the 5-substituent is a member of the group consisting of F, Cl, Br, I, CH=CH$_2$, C≡CH, C≡CHCH$_3$, CH=CHF, CH=CHCl, CH=CHBr, and CH=CHI.

2. A conformationally locked nucleoside analogue comprising the formula:

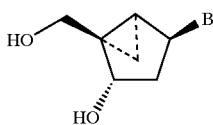

wherein B is uracil-1-yl having a 5-substituent, wherein the 5-substituent is bromine.

3. A conformationally locked nucleoside analogue comprising the formula:

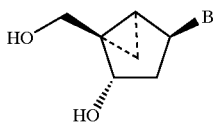

wherein B is uracil-1-yl having a 5-substituent, wherein the 5-substituent is iodine.

4. A conformationally locked nucleoside analogue comprising the formula:

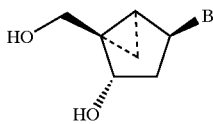

wherein B is uracil-1-yl having a 5-substituent wherein the 5-substituent is bromovinyl.

5. A pharmaceutical composition comprising the compound of claim 1 in a pharmaceutically acceptable excipient.

6. A pharmaceutical composition comprising the compound of claim 2 in a pharmaceutically acceptable excipient.

7. A pharmaceutical composition comprising the compound of claim 3 in a pharmaceutically acceptable excipient.

8. A pharmaceutical composition comprising the compound of claim 4 in a pharmaceutically acceptable excipient.

9. A method of reducing replication of a virus in an individual in need thereof, comprising the step of administering to said individual an effective antiviral amount of the compound of claim 1 in a pharmaceutically acceptable carrier, wherein the virus is selected from the group consisting of Herpes simplex virus HSV-1 and Herpes simplex virus HSV-2.

10. The method of claim 9, wherein said administering step is parenteral, enteral, topical, or sustained or directed release.

11. The method of claim 9, wherein said effective antiviral amount is about 100 mg to 500 mg per unit dosage.

12. A method of reducing replication of a virus in an individual in need thereof, comprising the step of administering to said individual an effective antiviral amount of the compound of claim 2 in a pharmaceutically acceptable carrier, wherein the virus is wherein said virus is selected from the group consisting of Herpes simplex virus HSV-1 and Herpes simplex virus HSV-2.

13. The method of claim 12, wherein said administering step is parenteral, enteral, topical, or sustained or directed release.

14. The method of claim 12, wherein said effective antiviral amount is about 100 mg to 500 mg per unit dosage.

15. A method of reducing replication of a virus in an individual in need thereof, comprising the step of administering to said individual an effective antiviral amount of the compound of claim 3 in a pharmaceutically acceptable carrier, wherein the virus is wherein said virus is selected from the group consisting of Herpes simplex virus HSV-1 and Herpes simplex virus HSV-2.

16. The method of claim 15, wherein said administering step is parenteral, enteral, topical, or sustained or directed release.

17. The method of claim 15, wherein said effective antiviral amount is about 100 mg to 500 mg per unit dosage.

18. A method of reducing replication of a virus in an individual in need thereof, comprising the step of administering to said individual an effective antiviral amount of the compound of claim 4 in a pharmaceutically acceptable carrier, wherein the virus is wherein said virus is selected from the group consisting of Herpes simplex virus HSV-1 and Herpes simplex virus HSV-2.

19. The method of claim 18, wherein said administering step is parenteral, enteral, topical, or sustained or directed release.

20. The method of claim 18, wherein said effective antiviral amount is about 100 mg to 500 mg per unit dosage.

21. A method of making the nucleoside analogue of claim 1 comprising the steps of:
reacting a bicyclo[3.1.0]hexane template with (E)-3-ethoxyacryloyl isocyanate to yield a first intermediate; and
reacting the first intermediate with H$_2$SO$_4$ in ethanol, whereby a bicyclo[3.1.0]hexane pyrimidine nucleoside intermediate is obtained;
reacting the bicyclo[3.1.0]hexane pyrimidine nucleoside intermediate with Br$_2$ in AcO$_2$ to yield a second intermediate; and
reacting the second intermediate with NH$_3$ in methanol, followed by NaOH in tetrahydrofuran, whereby the nucleoside analog of claim 1 is obtained.

22. A method of making the nucleoside analogue of claim 1 comprising the steps of:
reacting 5-iodo-3-phenylpyrimidine-2,4 (1H,3H)-dione with diethyl azodicarboxylate and PPh$_3$ in a solution of tetrahydrofuran, whereby a bicyclo[3.1.0]hexane pyrimidine nucleoside intermediate is obtained;
reacting the bicyclo[3.1.0]hexane pyrimidine nucleoside intermediate with NH$_4$OH in methanol, whereby a first intermediate is obtained; and
reacting the first intermediate with BCl$_3$ in methylene chloride, whereby the nucleoside analog of claim 1 is obtained.

23. A method of making the nucleoside analogue of claim 2 comprising the steps of:
reacting a bicyclo[3.1.0]hexane template with (E)-3-ethoxyacryloyl isocyanate to yield a first intermediate; and
reacting the first intermediate with $H_2SO_4$ in ethanol, whereby a bicyclo[3.1.0]hexane pyrimidine nucleoside intermediate is obtained;
reacting the bicyclo[3.1.0]hexane pyrimidine nucleoside intermediate with $Br_2$ in $AcO_2$ to yield a second intermediate; and
reacting the second intermediate with $NH_3$ in methanol, followed by NaOH in tetrahydrofuran, whereby the nucleoside analog of claim 6 is obtained.

24. A method of making the nucleoside analogue of claim 2 comprising the steps of:
reacting 5-iodo-3-phenylpyrimidine-2,4 (1H,3H)-dione with diethyl azodicarboxylate and $PPh_3$ in a solution of tetrahydrofuran, whereby a bicyclo[3.1.0]hexane pyrimidine nucleoside intermediate is obtained;
reacting the bicyclo[3.1.0]hexane pyrimidine nucleoside intermediate with $NH_4OH$ in methanol, whereby a first intermediate is obtained; and
reacting the first intermediate with $BCl_3$ in methylene chloride, whereby the nucleoside analog of claim 2 is obtained.

25. A method of making the nucleoside analogue of claim 3 comprising the steps of:
reacting a bicyclo[3.1.0]hexane template with (E)-3-ethoxyacryloyl isocyanate to yield a first intermediate; and
reacting the first intermediate with $H_2SO_4$ in ethanol, whereby a bicyclo[3.1.0]hexane pyrimidine nucleoside intermediate is obtained;
reacting the bicyclo[3.1.0]hexane pyrimidine nucleoside intermediate with $Br_2$ in $AcO_2$ to yield a second intermediate; and
reacting the second intermediate with $NH_3$ in methanol, followed by NaOH in tetrahydrofuran, whereby the nucleoside analog of claim 3 is obtained.

26. A method of making the nucleoside analogue of claim 3 comprising the steps of:
reacting 5-iodo-3-phenylpyrimidine-2,4 (1H,3H)-dione with diethyl azodicarboxylate and $PPh_3$ in a solution of tetrahydrofuran, whereby a bicyclo[3.1.0]hexane pyrimidine nucleoside intermediate is obtained;
reacting the bicyclo[3.1.0]hexane pyrimidine nucleoside intermediate with $NH_4OH$ in methanol, whereby a first intermediate is obtained; and
reacting the first intermediate with $BCl_3$ in methylene chloride, whereby the nucleoside analog of claim 3 is obtained.

27. A method of making the nucleoside analogue of claim 4 comprising the steps of:
reacting a bicyclo[3.1.0]hexane template with (E)-3-ethoxyacryloyl isocyanate to yield a first intermediate; and
reacting the first intermediate with $H_2SO_4$ in ethanol, whereby a bicyclo[3.1.0]hexane pyrimidine nucleoside intermediate is obtained;
reacting the bicyclo[3.1.0]hexane pyrimidine nucleoside intermediate with $Br_2$ in $AcO_2$ to yield a second intermediate; and
reacting the second intermediate with $NH_3$ in methanol, followed by NaOH in tetrahydrofuran, whereby the nucleoside analog of claim 4 is obtained.

28. A method of making the nucleoside analogue of claim 4 comprising the steps of:
reacting 5-iodo-3-phenylpyrimidine-2,4 (1H,3H)-dione with diethyl azodicarboxylate and $PPh_3$ in a solution of tetrahydrofuran, whereby a bicyclo[3.1.0]hexane pyrimidine nucleoside intermediate is obtained;
reacting the bicyclo[3.1.0]hexane pyrimidine nucleoside intermediate with $NH_4OH$ in methanol, whereby a first intermediate is obtained; and
reacting the first intermediate with $BCl_3$ in methylene chloride, whereby the nucleoside analog of claim 4 is obtained.

29. A method of testing the nucleoside analogue of claim 1 for antiviral activity comprising the step of measuring its effect in a cytopathogenic effect inhibition assay.

30. A method of testing the nucleoside analogue of claim 1 for antiviral activity comprising the step of measuring its effect in a virus plaque reduction assay.

31. A method of testing the nucleoside analogue of claim 2 for antiviral activity comprising the step of measuring its effect in a cytopathogenic effect inhibition assay.

32. A method of testing the nucleoside analogue of claim 2 for antiviral activity comprising the step of measuring its effect in a virus plaque reduction assay.

33. A method of testing the nucleoside analogue of claim 3 for antiviral activity comprising the step of measuring its effect in a cytopathogenic effect inhibition assay.

34. A method of testing the nucleoside analogue of claim 3 for antiviral activity comprising the step of measuring its effect in a virus plaque reduction assay.

35. A method of testing the nucleoside analogue of claim 4 for antiviral activity comprising the step of measuring its effect in a cytopathogenic effect inhibition assay.

36. A method of testing the nucleoside analogue of claim 4 for antiviral activity comprising the step of measuring its effect in a virus plaque reduction assay.

37. A pack comprising a conformationally locked nucleoside analogue in unit dosage form, wherein the conformationally locked nucleoside analogue comprises the formula:

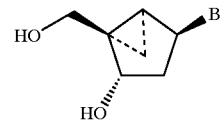

wherein B is uracil-1-yl having a 5-substituent or cytosin-1-yl having a 5-substituent, wherein the 5-substituent is selected from the group consisting of halogen, alkyl alkenyl, and alkynyl.

* * * * *

UNITED STATES PATENT AND TRADEMARK OFFICE
CERTIFICATE OF CORRECTION

PATENT NO. : 7,009,050 B2  Page 1 of 1
APPLICATION NO. : 10/346762
DATED : March 7, 2006
INVENTOR(S) : Marquez et al.

It is certified that error appears in the above-identified patent and that said Letters Patent is hereby corrected as shown below:

In Col. 15, Line 51, Claim 4, after "5-substituent" insert -- , --.

In Col. 17, Line 14, Claim 23, delete "claim 6" and insert -- claim 2 --.

In Col. 18, Line 57, Claim 37, after "alkyl" insert -- , --.

Signed and Sealed this

Twentieth Day of February, 2007

JON W. DUDAS
*Director of the United States Patent and Trademark Office*